United States Patent [19]

Imhof et al.

[11] 4,391,978

[45] * Jul. 5, 1983

[54] PHENYL-QUINOLIZIDINES

[75] Inventors: Rene Imhof, Gipf-Oberfrick; Emilio Kyburz, Reinach, both of Switzerland

[73] Assignee: Hoffmann-La Roche Inc., Nutley, N.J.

[*] Notice: The portion of the term of this patent subsequent to Nov. 25, 1997, has been disclaimed.

[21] Appl. No.: 252,540

[22] Filed: Apr. 9, 1981

Related U.S. Application Data

[63] Continuation-in-part of Ser. No. 186,936, Sep. 12, 1980, abandoned.

[30] Foreign Application Priority Data

Apr. 11, 1980 [CH] Switzerland ............... 2784/80
Feb. 3, 1981 [CH] Switzerland ............... 701/81

[51] Int. Cl.³ ............................................. C07D 455/02
[52] U.S. Cl. ..................................... 546/138; 424/267
[58] Field of Search ........................................... 546/138

[56] References Cited

U.S. PATENT DOCUMENTS

| | | | |
|---|---|---|---|
| 3,394,141 | 7/1968 | Sparatore | 546/138 |
| 3,692,791 | 9/1972 | Potoski et al. | 424/267 |
| 3,922,346 | 11/1975 | Bruderlein et al. | 424/258 |
| 3,948,923 | 4/1976 | Meyer et al. | 424/266 |
| 3,997,547 | 12/1976 | Alaimo | 424/256 |
| 4,213,983 | 7/1980 | Hadley et al. | 424/250 |
| 4,236,010 | 11/1980 | Imhof et al. | 546/138 |
| 4,272,627 | 6/1981 | Imhof et al. | 546/138 |
| 4,306,067 | 12/1981 | Imhof et al. | 546/138 |
| 4,316,030 | 2/1982 | Imhof et al. | 546/138 |
| 4,329,467 | 5/1982 | Imhof et al. | 546/138 |
| 4,338,444 | 7/1982 | Imhof et al. | 546/138 |

FOREIGN PATENT DOCUMENTS

| | | | |
|---|---|---|---|
| 37990 | 10/1981 | European Pat. Off. | 546/138 |
| 44573 | 1/1982 | European Pat. Off. | 546/138 |

OTHER PUBLICATIONS

J. Med. Chem. 1975, vol. 18, No. 2, pp. 185–188.

*Primary Examiner*—Ethel G. Love
*Attorney, Agent, or Firm*—Jon S. Saxe; Bernard S. Leon; William G. Isgro

[57] ABSTRACT

Phenyl-quinolizidines of the general formula

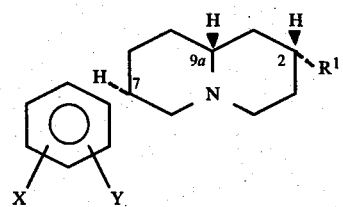

wherein X is hydrogen, fluorine, chlorine, lower-alkoxy, lower-alkyl or trifluoromethyl; Y is hydrogen, fluorine, chlorine, lower-alkoxy or lower-alkyl; and $R^1$ is acyl, acylamino or a group A of the formula

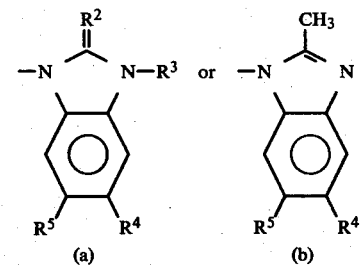

wherein $R^2$ is oxygen or sulfur; $R^3$ is hydrogen or lower-alkyl; and one of $R^4$ and $R^5$ is hydrogen and the other is bromine, iodine, cyano, lower-alkoxycarbonyl or sulfamoyl, as racemates or enatiomers, as well as acid addition salts thereof, utilizing various intermediates, are described. The foregoing compounds are useful as neuroleptic, antiemetic and analgesic agents.

5 Claims, No Drawings

PHENYL-QUINOLIZIDINES

CROSS-REFERENCE TO RELATED APPLICATIONS

This application is a continuation-in-part of application Ser. No. 186,936, filed Sept. 12, 1980, now abandoned.

BRIEF SUMMARY OF THE INVENTION

The invention relates to pharmacologically active phenyl-quinolizidines, their preparation and use, intermediate products in the preparation of said phenyl-quinolizidines and medicaments containing said phenyl-quinolizidines.

More particularly, the phenyl-quinolizidines of the invention are characterized by the formula

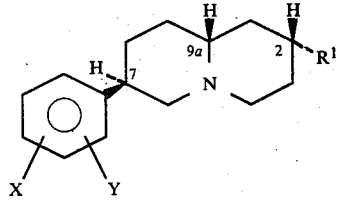

I wherein X is hydrogen, fluorine, chlorine, lower-alkoxy, lower-alkyl or trifluoromethyl; Y is hydrogen, fluorine, chlorine, lower-alkoxy or lower-alkyl; and $R^1$ is acyl, acylamino or a group A of the formula

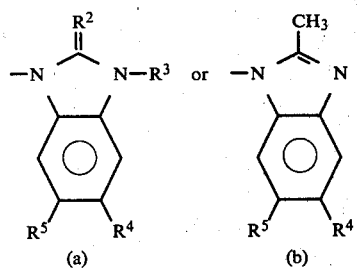

wherein $R^2$ is oxygen or sulfur; $R^3$ is hydrogen or lower-alkyl; and one of $R^4$ and $R^5$ is hydrogen, and the other is bromine, iodine, cyano, lower-alkoxycarbonyl or sulfamoyl, in the form of the racemate or the enantiomers, as well as acid addition salts of such compounds.

In another aspect the invention relates to intermediates of the formulas

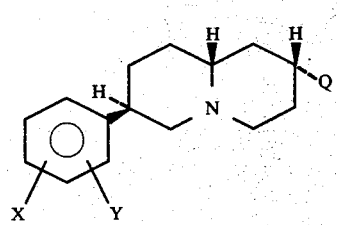

V

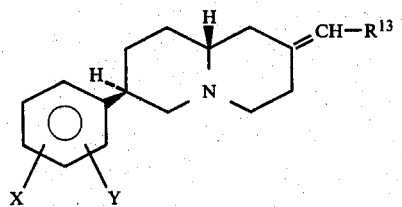

VI

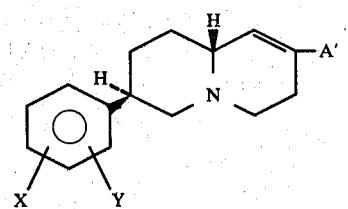

VII

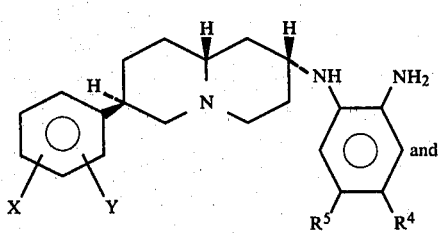

VIII and

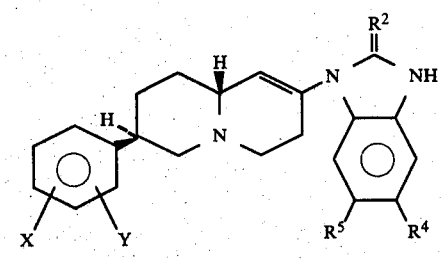

XIII wherein A', Q, $R^2$, $R^4$, $R^5$, $R^{13}$, X, and Y are as hereinafter described.

DETAILED DESCRIPTION OF THE INVENTION

The phenyl-quinolizidines of the invention are characterized by the formula

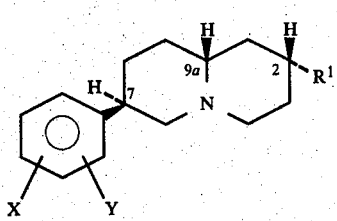

I wherein X is hydrogen, fluorine, chlorine, lower-alkoxy, lower-alkyl or trifluoromethyl; Y is hydrogen, fluorine, chlorine, lower-alkoxy or lowr-alkyl; and $R^1$ is acyl, acylamino or a group A of the formula

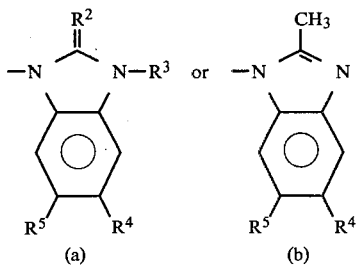

(a)     (b)

wherein $R^2$ is oxygen or sulfur; $R^3$ is hydrogen or lower-alkyl; and one of $R^4$ and $R^5$ is hydrogen and the other is bromine, iodine, cyano, lower-alkoxycarbonyl or sulfamoyl,
as racemate or corresponding enantiomers, as well as acid addition salts of such compounds.

As indicated in formula I and in various of the formulas which follow, the hydrogen atoms in positions 7 and 9a or 7 and 2 are trans-positioned to one another, so that, in the formulas the 9a- and 2-hydrogen atoms are arbitrarily indicated in the β-position and the 7-hydrogen atom is correspondingly indicated in the α-position. The quinolizidines of formula I of the invention, as well as also the corresponding intermediate products and starting materials, are, however, not limited to this absolute configuration, but also embrace the corresponding enantiomeric forms, namely compounds with hydrogen in 9aα,2α and 7β, as well as the racemates of these two enantiomeric forms.

As used herein, lower-alkyl or lower-alkoxy denotes a group which contains 1–6 carbon atoms, especially 1–4 carbon atoms, whereby the groups with 3 and more carbon atoms can be straight-chain or branched. The acyl residue contained in the acylamino groups $R^1$ can be derived from organic, saturated, optionally substituted carboxylic acids, for example from lower alkanecarboxylic acids of 1–6 carbon atoms, such as acetic acid or propionic acid; from lower cycloalkanecarboxylic acids with 4–7 C-atoms, such as cyclopropanecarboxylic acid, cyclohexanecarboxylic acid; from benzoic acid which can be substituted, for example, by halogen, amino, lower-alkoxy, sulfamoyl and/or lower-alkylsulfonyl, for example, by 4-fluoro, by 2-methoxy-4-amino-5-chloro, by 2-methoxy-5-sulfamoyl or by 2-methoxy-5-ethylsulfonyl; from aromatic or cycloaliphatic heterocyclocarboxylic acids with at least one oxygen, sulfur or nitrogen atom in the ring, for example, from furan-2-carboxylic acid, thiophene-2-carboxylic acid, 2-oxo-1-pyrrolidine carboxylic acid. Acylamino groups set forth in $R^1$ can be optionally substituted on the nitrogen, for example, by lower alkyl or phenyl.

Acyl residues set forth in $R^1$ have an analogous significance as given above for the acyl residues contained in acylamino groups set forth in $R^1$.

As acid addition salts of tthe phenyl-quinolizidines of formula I of the invention, there come into consideration pharmacologically or pharmaceutically compatible salts with organic and inorganic acids customarily used for salt formation. Examples of such acids are mineral acids, such as, sulfuric acid, nitric acid, phosphoric acid, hydrohalic acids, for example, hydrochloric acid or hydrobromic acids; organic acids, such as tartaric acid, citric acid, aliphatic or aromatic sulfonic acids, maleic acid, mandelic acid and the like. The salt formation can be carried out in a known manner.

Sub-groups within formula I are:
(a) carboxamides of the formula

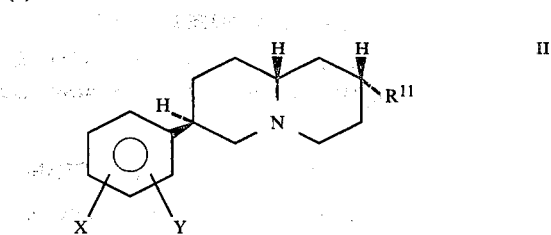

whereby X and Y are as previously described and $R^{11}$ is acylamino,
in racemic form and in the form of the corresponding enantiomers, as well as optionally in the form of acid addition salts,
(b) ketones of the formula

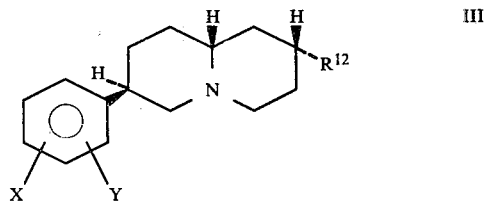

wherein X and Y are as previously described, and $R^{12}$ is acyl,
in racemic form and in the form of the corresponding enantiomers, as well as optionally in the form of acid addition salts,
(c) benzimidazolinone (and -thione) derivaties of the formula

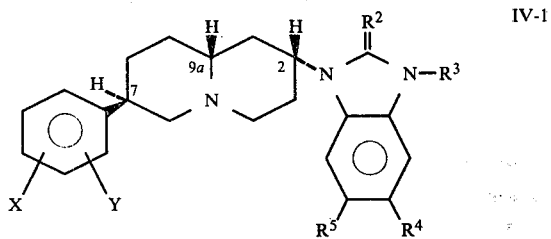

wherein X, Y and $R^2$–$R^5$ are as previously described, in racemic form and in the form of the corresponding enantiomers, as well as optionally in the form of acid addition salts,
(d) methylbenzimidazole derivatives of the formula

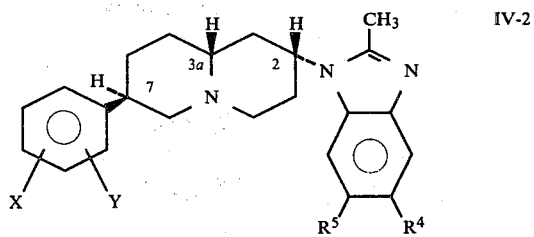

wherein X, Y, $R^4$ and $R^5$ are as previously described in racemic form and in the form of the corresponding enantiomers, as well as optionally in the form of acid addition salts.

The compounds of formula I possess useful pharmacological properties. Thus, neuroleptic, antiemetic and/or analgesic activities have been established. Especially preferred, due to their pharmacological activities, are compounds of formula I wherein X is hydrogen and Y is o-chloro or o-fluoro. Neuroleptic activity is present in the ketones of formula III, especially, wherein $R^{12}$ is p-fluorobenzoyl. The carboxamides of formula II, especially wherein $R^{11}$ is cyclopropanecarboxamide, 2-thiophenecarboxamido, 2-oxo-1-pyrrolidinecarboxamido or p-fluorobenzamido, are likewise neuroleptically active. The benzimidazolinone (and thione) derivatives of formula IV, especially wherein $R^4$ is bromine, iodine or cyano and $R^5$ is hydrogen, as well as also the methyl-benzimidazole derivatives of formula IV-2 are likewise neuroleptically active. Carboxamides of formula II wherein $R^{11}$ is sulfamoylbenzamido or lower-alkylsulfonylbenzamido, especially 5-sulfamoyl-o-anisamido or 5-ethylsulfonyl-o-anisamido, are antiemetically active. Carboxamides of the formula

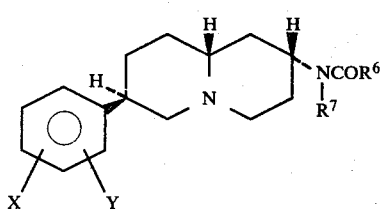

II-1 wherein X and Y is as previously described, $R^6$ is lower alkyl, preferably ethyl, and $R^7$ is lower alkyl or, preferably, phenyl, or phenyl substituted by halogen, lower alkyl or lower alkoxy,
are analgesically active.

Particularly preferred compounds are:
Neuroleptically active:
rac-1-[(9aβH)-7β-(o-fluorophenyl)-octahydro-2H-quinolizin-2α-yl]-5-bromo-2-benzomidazolinone,
rac-1-[(9aβH)-7β-(o-fluorophenyl)-octahydro-2H-quinolizin-2α-yl]-5-iodo-2-benzimidazolinone,
rac-1-[(9aαH)-7β-(o-fluorophenyl)-octahydro-2H-quinolizin-2α-yl]-5-cyano-2-benzimidazolinone,
rac-4-amino-5-chloro-N-[(9aβH)-7β-(o-chlorophenyl)-octahydro-2H-quinolizin-2α-61]-o-anisamide,
rac-N-[(9aβH)-7β-(o-chlorophenyl)-octahydro-2H-quinolizin-2α-yl]-5-(ethylsulphonyl)-o-anisamide,
rac-N-[(9aβH)-7β-(o-chlorophenyl)-octahydro-2H-quinolizin-2α-yl]-p-fluorobenzamide,
rac-N-[(9aβH)-7β-(o-chlorophenyl)-octahydro-2H-quinolizin-2α-yl]-cyclopropanecarboxamide,
rac-N-[(9aβH)-7β-(o-chlorophenyl)-octahydro-2H-quinolizin-2α-yl]-2-thiophenecarboxamide,
rac-N-[(9-aβH)-7β-(o-chlorophenyl)-octahydro-2H-quinolizin-2αyl]-2-oxo-1-pyrrolidinecarboxamide,
rac-[(9aβH)-7β-(o-chlorophenyl)-octahydro-2H-quinolizin-2α-yl]p-fluorophenylketone.

Antiemetically active:
rac-N-[(9aβH)-7β-(o-chlorophenyl)-octahydro-2H-quinolizin-2α-yl]-5-sulfamoyl-o-anisamide,
rac-4-amino-5-chloro-N-[(9aβH)-7β-(o-chlorophenyl)-octahydro-2H-quinolizin-2α-yl]-o-anisamide,
rac-N-[(9aβH)-7β-(o-chlorophenyl)-octahydro-2H-quinolizin-2α-yl]-5-(ethylsulfonyl)o-anisamide.

Analgesically active:
rac-N-[(9aβH)-7β-(o-chlorophenyl)-octahydro-2H-quinolizin-2α-yl]-propionanilide,
rac-4'-chloro-N-[(9aβH)-7β-(o-chlorophenyl)-octahydro-2H-quinolizin-2α-yl]-propionanilide.
rac-3'-chloro-N-[(9aβH)-7β-(o-chlorophenyl)-octahydro-2H-quinolizin-2α-yl]-propionanilide,
rac-N-[(9aβH)-7β-(o-fluorophenyl)-octahydro-2H-quinolizin-2α-yl]-propionanilide,
rac-4'-fluoro-N-[(9aβH)-7β-(o-fluorophenyl)-octahydro-2H-quinolizin-2α-yl]-propionanilide,
rac-4'-fluoro-N-[(9aβH)-7β-phenyl-octahydro-2H-quinolizin-2α-yl]-propionanilide,
rac-N-[(9aβH)-7β-(o-fluorophenyl)-octahydro-2H-quinolizin-2α-yl]-acetanilide,
rac-N-[(9aβH)-7β-(o-chlorophenyl)-octahydro-2H-quinolizin-2α-yl]-N-butylpropionamide,
rac-N-[9aβH)-7β-phenyl-octahydro-2H-quinolizin-2α-yl]-propionanilide.

The phenyl-quinolizidine of formula I are prepared in accordance with the invention by the following process:

1. To prepare carboxamides of the formula

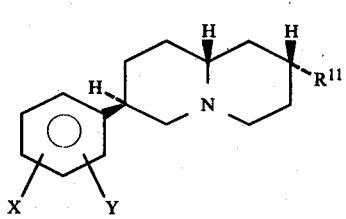

II wherein X and Y are as previously described and $R^{11}$ is acylamino,
a primary or secondary amine of the formula

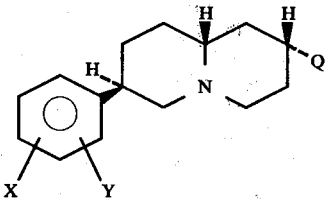

V wherein X and Y are as previously described and Q is a primary or secondary amino group,
is acylated, or in that 2. To prepare ketones of the formula

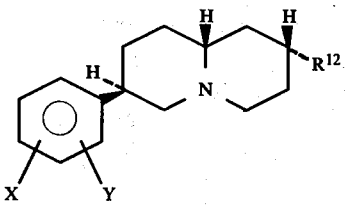

III wherein X and Y are as previously described and $R^{12}$ is acyl,
a compound of the formula

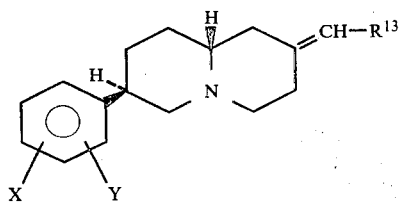

wherein X and Y are as previously described and the ylidene group =CH—R$^{13}$ corresponds to the acyl residue R$^{12}$ wherein the oxo function has been exchanged by hydrogen,
is treated with diborane and hydrogen peroxide and the carbinol obtained is subjected to an oxidation, or 3. To prepare a compound of the formula

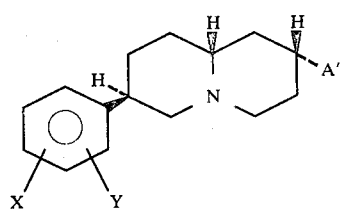

wherein X and Y are as previously described and A' is A, except that R$^2$ is oxygen, and R$^4$ and R$^5$ are other than bromine and iodine,
a compound of the formula

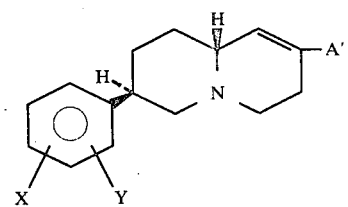

wherein X, Y and A' are as previously described, is catalytically hydrogenated, or 4. To prepare a compound of the formula

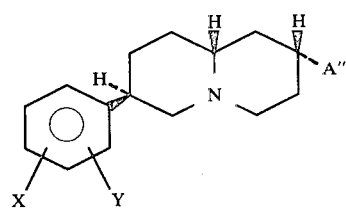

wherein X and Y are as previously described and A" is A, except that R$^2$ is oxygen and R$^3$ is hydrogen, a phenylene-diamine of the formula

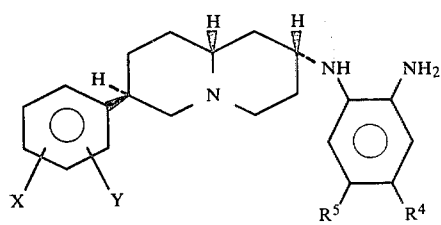

wherein X,Y,R$^4$ and R$^5$ are as previously described, is condensed with a cyclizing agent of the formula

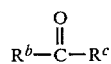

wherein R$^b$ and R$^c$ are halogen, amino or 1-imidazolyl, or with acetic acid or an orthoacetic acid ester, or 5. To prepare compounds of the formula

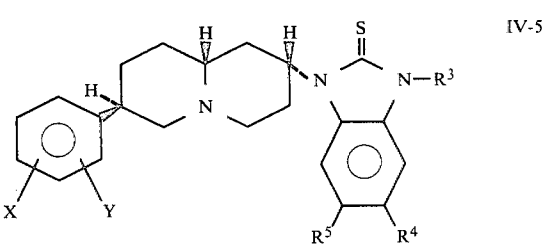

wherein X, Y and R$^3$–R$^5$ are as previously described, either (a) a corresponding oxo compound of the formula

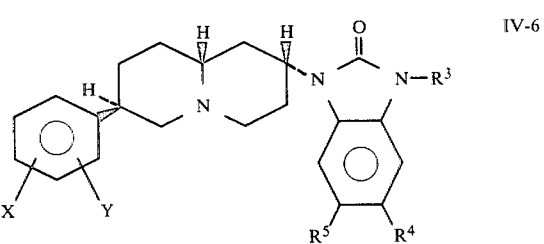

wherein X, Y and R$^3$–R$^5$ are as previously described, is reacted with P$_2$S$_5$, or (b) a phenylene-diamine of the formula X, described hereinafter, is reacted with thiophosgene, thiocarbonyldiimidazole or CS$_2$ and subsequently optionally N-alkylated, or 6. Compounds of the general formula

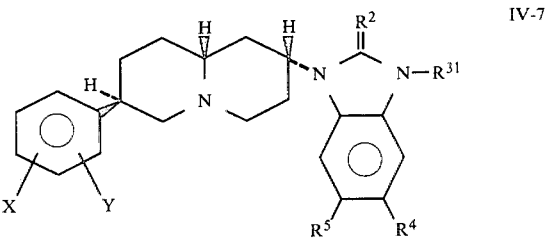

wherein X, Y, R$^2$, R$^4$ and R$^5$ are as previously described and R$^{31}$ is lower-alkyl,
a compound of the formula

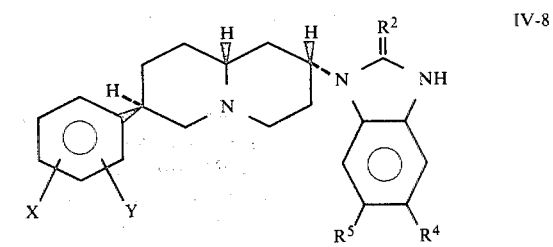

wherein X, Y, R², R⁴ and R⁵ are as previously described,
is N-alkylated, and in that racemates obtained are optionally resolved and bases obtained are optionally converted into acid addition salts.

All of the reactions named in the foregoing process variants 1–6 can be carried out according to known methods.

For the acylation of a primary or secondary amine V, in accordance with process variant 1, there come into consideration agents customarily used for acylation reactions, for example, a reactive derivative of the corresponding carboxylic acid, for example, the corresponding acid halide, preferably, the acid chloride, acid anhydride, preferably, a mixed anhydride, for example, with chloroformic acid ethyl ester, or the corresponding acid ester, for example, the methyl or ethyl ester. The reaction is advantageously effected in the presence of an acid-binding agent, for example, triethylamine, pyridine or alkali metal carbonate. It can likewise be acylated with the corresponding carboxylic acid in the presence of a dehydrating agent, such as dicyclohexylcarbodiimide. As the solvent for the acylation there come into consideration the usual inert solvents, for example, benzene, toluene or diethyl ether. The reaction temperature is not critical and preferably lies in the range of from about 0° C. to the boiling point of the reaction mixture.

For the preparation of ketones of formula III, an ylidene compound of formula VI is treated first with diborane, thereafter the addition product is oxidatively worked-up with hydrogen peroxide to the corresponding carbinolic epimer mixture and the latter is oxidized to the ketone. The diborane is preferably generated in situ in a known manner, for example, from an alkali metal borohydride and boron trifluoride etherate in an ethereal solvent, such as, ethyleneglycol dimethyl ether, at a temperature in the range of from about −20° C. to +50° C. For the oxidation of the carbinol to the ketone there is used a usual inorganic or organic oxidation agent, for example, chromium trioxide, manganese dioxide, alkali metal permanganate, silver carbonate or dimethyl sulfoxideacetic anhydride-triethylamine. The ketone of formula V is obtained as the epimer mixture (2αH+2βH). If desired, this mixture can be transformed into the more stable 2βH-epimer by treatment with an alkali metal alcoholate. The oxidation is carried out in an inert solvent, for example, in acetone; the subsequent epimerization is preferably effected in an alcoholic solvent, for example, in a lower alkanol. The reaction temperature for the oxidation or the epimerization preferably lies in the range of from about 0° C. to the boiling point of the reaction mixture.

For the preparation of the benzimidazole derivatives of formula IV-3 according to process variant 3, the Δ¹-double bond of the compound of formula VII can be catalytically hydrogenated. As the catalysts, there can be used usual hydrogenation catalysts, such as PtO₂ or Pd/C for example.

For the preparation of the benzimidazole derivaties of formula IV-4 according to process variant 4, a phenylenediamine of formula VIII can be condensed with a cyclizing agent of formula IV, for example, phosgene, carbonyldiimidazole or urea, whereby there results a benzimidazolinone derivative of formula IV-1, or also with acetic acid or an orthoacetic acid ester, for example, the trimethyl or triethyl ester, whereby there is obtained a methylbenzimidazole derivative of formula IV-2.

For the preparation of the thiones of formula IV-5, the oxygen of the imidazole ring of an oxo compound of formula IV-6 can either be exchanged for sulfur with P₂S₅ in accordance with process variant 5a according to known methods, or a phenylenediamine of formula VIII can be reacted with thiophosgene, thiocarbonyldiimidazole or CS₂ in accordance with process variant 5b in a known manner. The subsequent, facultative N-alkylation at R³ is effected as indicated hereinafter for process variant 6.

The process variants 4 and 5b are especially well suited to the preparation of compounds of formula IV-4 or IV-5 wherein R⁴ is different from R⁵.

For the preparation of compounds of formula IV-7 which are N-alkylated in the imidazole ring according to process variant 6, a usual N-alkylating agent, for example, a lower-alkyl halide, such as methyl iodide, can be used.

A lower-alkoxycarbonyl group R⁴ or R⁵ present in the end product can be optionally saponified to the carboxy group. For this purpose, the usual acidic, for example, mineral acidic, or basic agents, for example, aqueous alkali hydroxide are suitable. Mineral acid is preferred, for example, heating with aqueous hydrochloric acid. The temperature is, however, not critical, it can be, for example, in the range of about room temperature to the boiling point of the reaction mixture.

The compounds referred to in the following as intermediate products or starting materials, insofar as they are not known, can be prepared according to known methods. Thus, for example, the primary amines of formula V used as the starting material in process variant 1 can be obtained in a known manner by oximation of a ketone of the formula

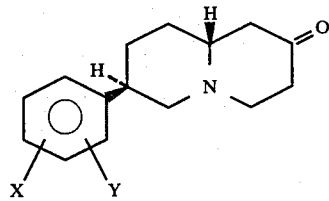

wherein X and Y are as previously described, with hydroxylamine hydrochloride and reduction of the oxime obtained to the amine by hydrogenation with a noble metal catalyst, such as, Raney-nickel. The secondary amines of formula V are obtained, for example, by subjecting the ketone of formula X to a reductive amination with a primary amine. As the primary amine there come into consideration, preferably, aniline and lower alkylamines, such as, methyl- or ethylamine. As the reducing agent there is used in particular an alkali metal cyanoborohydride, for example, sodium cyanoborohydride. The preferred 2βH-epimer can be separated chromatographically from an obtained diastereomer mixture of an amine of formula V or also by fractional crystallization of corresponding addition salts, for example, the hydrochloride.

The ketone X, in turn, can be obtained by decarboxylation of β-keto-esters of formula XI with the relative configuration with respect to the positions 1, 7 and 9a indicated in the following formula

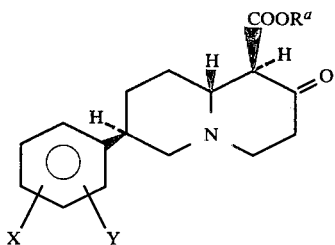

wherein X and Y are as previously described and R^a is lower-alkyl, see for instance Example 1e.

The β-keto-esters of formula XI can, in turn, be obtained from the corresponding unsaturated β-ketoesters of formula

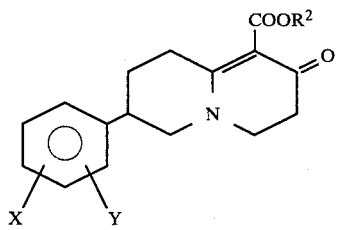

wherein X, Y and R^a are as previously described, in a known manner by hydrogenation, see for instance Example 1f.

The esters of formula XII can be obtained from corresponding 5-phenyl-2-piperidones which are optionally substituted in the phenyl according to known methods, for instance Example 1g.

The ylidene compounds of formula VI referred to as the starting material in process variant 2 are obtained from the ketones of formula X via a Wittig reaction with a compound of the formula $R^{13}CH_2P$ (phenyl)$_3{}^+Cl^-$ and n-butyl lithium, for example according to the details in Example 7.

The phenylenediamines of formula VIII used in process variant 4 are obtained by reaction of a primary amine V with a correspondingly substituted o-halonitrobenzene, preferably an o-chloro- or o-fluoro-nitrobenzene derivative and reduction of the nitro group to amino, for example, with hydrochloric acid and iron powder.

The benzimidazolinones of formula IV-8 referred to as the starting material in process variant 6 can be obtained by hydrogenation from the corresponding unsaturated compounds of formula XIII, with the relative configuration in the positions 7 and 9a indicated in the following formula,

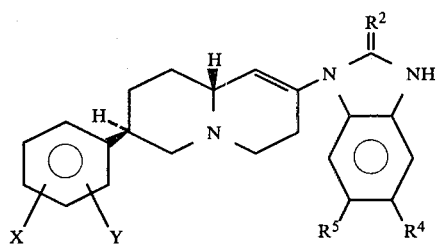

wherein X, Y, $R^2$, $R^4$ and $R^5$ are as previously described.

By N-alkylation of a compound of formula XIII as in process variant 6 there are obtained N-alkylated starting compounds of formula VII, for use in process variant 3.

The compounds of the formula XIII can, in turn, be obtained from the β-ketoesters XI by heating with a diamine of the formula

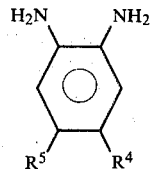

wherein $R^4$ and $R^5$ are as previously described.

The intermediate products or starting materials of formulas V, VI, VII and VIII also form part of the invention.

The phenyl-quinolizidines of formula I in accordance with the invention distinguish themselves by their valuable pharmacological properties. The compounds of formula I have neuroleptic, central-depressant, tranquilizing, antiemetic and/or analgesic activity and can accordingly find use as antipsychotics or antiemetics or analgesics in the control of psychoses and neuroses or of nausea or of pain.

The neuroleptic properties of the compounds of formula I can be demonstrated numerically with the tests described hereinafter:

"Pole Climbing" Test (rat)

For this experimental procedure there was used per dosage a group of 10 rats trained to jump up on a vertical isolated pole in the experimental cage, to escape an electroshock (unconditioned stimulus) produced via the lattice floor immediately after an acoustic signal (conditioned stimulus). The inhibition of the conditioned reaction in the case of 50% of the animals during an observation time of 6 hours is determined by the parameter ED 50 BCR, the inhibition of the unconditioned reaction is determined by the parameter ED 10 BUR.

Spiroperidol-Binding Test (in vitro)

In the in vitro experiments calf striatum was used as the receptor (Lit.: Creese et al., Life Sci. 17, 993 (1975) and incubated with [$^3$H]-spiroperidol analogously to the method described by Fields et al., Brain Research 136, 578 (1977). With a computer program, there was determined from 4 different concentrations in a triple procedure the IC 50 which gives the concentration of the test substance at which a 50% detachment of the specific binding of [$^3$H]-spiroperidol on the receptor takes place.

Experimental results are compiled in Table A which follows:

TABLE A

| | Pole-Climbing | | Spiroperidol- |
| | BCR | BUR | Binding |
| | $ED_{50}$ i.p. | $ED_{10}$ i.p. | $IC_{50}$ |
| Compound | (mg/kg) | (mg/kg) | (nanomolar) |
| rac-1-[(9aβH)—7β-(o-Fluorophenyl)-octahydro-2H—quinolizin-2α-yl]-5-bromo-2-benzimidazolinone. HCl | 0.08 | 0.1 | 3.8 |
| rac-1-[(9aβH)—7β-(o-Fluorophenyl)-octahydro-2H—quinolizin-2α-yl]-5-iodo-2-benzimidazolinone. | | | |

TABLE A-continued

| Compound | Pole-Climbing BCR ED$_{50}$ i.p. (mg/kg) | Pole-Climbing BUR ED$_{10}$ i.p. (mg/kg) | Spiroperidol-Binding IC$_{50}$ (nanomolar) |
|---|---|---|---|
| HCl rac-1-[(9aβH)—7β-(o-Fluorophenyl)-octahydro-2H—quinolizin-2α-yl]-5-cyano-2-benzimidazolinone. | 0.1 | 0.055 | 8.6 |
| HCl rac-4-Amino-5-chloro-N—[(9aβH)—7β-(o-chlorophenyl)-octahydro-2H—quinolizin-2α-yl]-o-anisamide | 0.65 | 1.0 | 50 |
| rac-N—[(9aβH)—7β-(o-Chlorophenyl)-octahydro-2H—quinolizin-2α-yl]-5-(ethylsulfonyl)-o-anisamide | 12.5 | 12.5 | 30 |
| rac-N—[(9aβH)—7β-(o-Chlorophenyl)-octahydro-2H—quinolizin-2α-yl]-p-fluorobenzamide | 10.0 | 10.0 | 135 |
| rac-N—[(9aβH)—7β-(o-Chlorophenyl)-octahydro-2H—quinolizin-2α-yl]-cyclopropanecarboxamide | 12.0 | 5.5 | 67 |
| rac-N—[(9aβH)—7β-(o-Chlorophenyl)-octahydro-2H—quinolizin-2α-yl]-2-thiophenecarboxamide | 6.0 | 5.5 | 550 |
| rac-N—[(9aβH)—7β-(o-Chlorophenyl)-octahydro-2H—quinolizin-2α-yl]-2-oxo-1-pyrrolidine-carboxamide | 18.0 | 25.0 | 123 |
| rac-[(9aβH)—7β-(o-Chlorophenyl)-octahydro-2H—quinolizin-2α-yl]p-fluorophenyl ketone | 23.0 | >30 | |
| | 3.0 | 3.0 | 11 |

The analgesic properties of the compounds were determined numerically utilizing the tests described hereinafter:

Writhing Test (mouse)

To carry out the experiment, there were employed 8 male mice (20–22 g) per dosage. Sixty (60) minutes after effecting oral administration of the test substance, 10 ml/kg of the test solution was injected intraperitoneally into the test animals. Following a latent period of 5 minutes, the number of animals in which over a period of 5 minutes no more than 1 characteristic writhing symptom (convulsive stretching movement of the body) occurred was registered. The ED 50 gives that dosage at which 50% of the animals show no more than 1 writhing.

Experimental results are compiled in Table B which follows:

TABLE B

| Compound | Writhing 60' ED$_{50}$ p.o. (mg/kg) |
|---|---|
| rac-N—[(9aβH)—7β-(o-Chlorophenyl)-octahydro-2H—quinolizin-2α-yl]-propionanilide | 0.12 |
| rac-4'-Chloro-N—[(9aβH)—7β-(o-chlorophenyl)-octahydro-2H—quinolizin-2α-yl]-propionanilide | 1.3 |
| rac-3'-Chloro-N—[(9aβH)—7β-(o-chlorophenyl)-octahydro-2H—quinolizin-2α-yl]-propionanilide | 0.95 |
| rac-N—[(9aβH)—7β-(o-Fluorophenyl)-octahydro-2H—quinolizin-2α-yl]-propionanilide | 0.08 |
| rac-4'-Fluoro-N—[(9aβH)—7β-(o-Fluorophenyl)-octahydro-2H—quinolizin-2α-yl]-propionanilide | 0.17 |
| rac-4'Fluoro-N—[(9aβH)—7β-phenyl-octahydro-2H—quinolizin-2α-yl]-propionanilide | 0.006 |

Antiemetic Activity (dog)

A subcutaneous dosage of 0.1 or 0.3 mg of apomorphine hydrochloride/kg body weight (0.1% or 0.3% solution, solvent 0.9% sodium chloride-water) was administered to pure-bred female Beagle hounds, 12–15 kg, 3 animals per dosage. For the test, only those animals which showed at least an average four-fold vomiting during the hour after apomorphine administration in 3 separate experiments (in two-week intervals) were selected. The test compound was administered orally. One (1) hour after administration of the test substance, apomorphine hydrochloride was injected subcutaneously in the calculated amount of 0.1 or 0.3 mg/kg body weight. The presence or absence of vomiting was observed during the next hour. The ED$_{50}$ is defined as that dosage at which 50% of the animals are protected against apomorphine-induced vomiting.

Experimental results are compiled in Table C which follows:

TABLE C

| Compound | Anti-apomorphine emesis ED$_{50}$ p.o. (mg/kg) |
|---|---|
| rac-N—[(9aβH)—7β-(o-Chlorophenyl)-octahydro-2H—quinolizin-2α-yl]-5-sulfamoyl-o-anisamide | 0.8 |
| rac-4-Amino-5-chloro-N—[(9aβH)—7β-(o-chlorophenyl)-octahydro-2H—quinolizin-2α-yl]-o-anisamide | 2.3 |
| rac-N—[(9aβH)—7β-(o-chlorophenyl)-octahydro-2H—quinolizin-2α-yl]-5-(ethylsulfonyl)-o-anisamide | 0.38 |

The compounds of formula I of the invention in the form of the racemate or of the enantiomers, as well as in the form of the free bases, as well as of acid addition salts, find use as medicaments, for example, in the form of pharmaceutical preparations. The pharmaceutical preparations can be administered orally, for example, in the form of tablets, coated tablets, dragees, hard and soft gelatin capsules, solution, emulsions or suspensions. The administration can, however, also be effected rectally, for example, in the form of suppositories, locally or percutaneously, for example, in the form of salves, creams, gels, solutions, or parenterally, for example, in the form of injectable solutions.

To prepare tablets, coated tablets, dragees and hard gelatin capsules, the compounds in accordance with the invention can be admixed with pharmaceutically inert, inorganic or organic excipients. Such excipients include, for example, for tablets, dragees and hard gelatin capsules, lactose, maize starch or derivatives thereof, talc, stearic acid or salts thereof and the like. For soft gelatin capsules, suitable excipients are, for example, vegetable oils, waxes, fats, semi-solid, liquid polyols, and the like. Depending on the nature of the active substance, no excipients are generally required, however, in the case of soft gelatin capsules. To prepare solutions and syrups, suitable excipients are, for example, water, polyols, saccharose, invert sugar, glucose and the like. To prepare injection, suitable excipients are, for example, water, alcohols, polyols, glycerine, vegetable oils and the like. To prepare suppositories, local or percutaneous application forms, suitable excipients are, for examples, natural or hardened oils, waxes, fats, semi-liquid, liquid polyols and the like.

The pharmaceutical preparations can, moreover, also contain preserving agents, solubilizing agents, stabilizing agents, wetting agents, emulsifying agents, sweetening agents, coloring agents, flavoring agents, salts for varying the osmotic pressure, buffers, coating agents or antioxidants. The pharmaceutical preparations can also contain still other therapeutically valuable substances.

The foregoing pharmaceutical preparations can contain doses of a compound of formula I in the range of from 0.5 to 100 mg. In the case of oral application, a compound of formula I can be in the range of from about 0.05 mg/kg to about 10 mg/kg per day and in the case of parenteral application in the range of from about 0.01 mg/kg to 1 mg/kg per day.

The examples which follow further illustrate the invention. All temperatures are in degrees centigrade, unless otherwise described.

EXAMPLE I

Preparation of rac-1-[(9aβH)-7β-(o-fluorophenyl)-octahydro-2H-quinolizin-2α-yl-5-iodo-2-benzimidazolinone.

(a) A solution of 4.80 g of rac-(9aβH)-7β-(o-fluorophenyl)octahydro-2α-(2-amino-4-iodo-anilino)-2H-quinolizine in 80 ml of methylene chloride is treated with 3.0 g of N,N'-carbonyl-diimidazole (93%) and stirred at room temperature overnight. The precipitated reaction product is filtered off after 20 hours, washed with 3×100 ml of methylene chloride and subsequently dried. There is obtained crystalline rac-1-[(9aβH)-7β-(o-fluorophenyl)-octahydro-2H-quinolizin-2α-yl]-5-iodo-2-benzimidazolinone. M.p. 271°–274° C. The hydrochloride melts at 265°–267° C.

When in place in rac-(9aβH)-7β-(o-fluorophenyl)-octahydro-2α-(2-amino-4-iodo-anilino)-2H-quinolizine correspondingly substituted phenylenediamines are reacted with N,N'-carbonyl-diimidazole, one proceeds to the following products:
rac-1-[(9aβH)-7β-(R$_a$)octahydro-2H-quinolizin-2α-yl]-(B)-2-benzimidazolinone:

|  |  |  |  | M.p. °C. |
|---|---|---|---|---|
| R$_a$ = | o-fluorophenyl | B = | 5-bromo | 296–299 (HCl salt) |
|  | o-fluorophenyl | B = | 5-ethoxy-carbonyl | 277–280 (HCl salt) |
|  | o-fluorophenyl | B = | 5-cyano | 300 (HCl salt) |
|  | o-fluorophenyl | B = | 5-sulfamoyl | 290–295 (base) |

(b) The rac-(9aβH)-7β-(o-fluorophenyl)octahydro-2α-(2-amino-4-iodoanilino)-2H-quinolizine used as the starting material in Example 1a can be obtained as follows:

5.1 g of rac-(9aβH)-7β-(o-fluorophenyl)octahydro-2α-(2-nitro-4-iodoanilino)-2H-quinolizine are heated under reflux conditions for 4 hours in 100 ml of methanol, 2.0 ml of conc. hydrochloric acid and 1.75 g of iron powder. Subsequently, the reaction mixture is partitioned between 0.5 N sodium hydroxide and chloroform. The chloroform extracts are dried over anhydrous sodium carbonate and then evaporated. From ethanol-n-hexane there crystallizes the rac-(9aβH)-7β-(o-fluorophenyl)octahydro-2α-(2-amino-4-iodo-anilino)-2H-quinolizine. M.p. 106°–110° C.

rac-(9aβH)-7β-(o-Fluorophenyl)octahydro-2α-(2-amino-4-bromoanilino)-2H-quinolizine, m.p. 153°–155° C., can be manufactured analogously, likewise the corresponding

| 4-carbonitrile | m.p.: 190–193° C. |
|---|---|
| 4-sulfonic acid amide | m.p.: 226–228° C. |
| 4-carboxylic acid ethyl ester | m.p.: 149–156° C. |

(c) The rac-(9aβH)-7β-(o-fluorophenyl)octahydro-2α-(2-nitro-4-iodoanilino)-2H-quinolizine employed as the starting material in Example 1b can be obtained as follows:

7.5 g of rac-(9aβH)-7β-(o-fluorophenyl)-2α-(amino)octahydro-2H-quinolizine are dissolved in 75 ml of cyclohexanol (99%), treated with 6.40 g of sodium carbonate (anhydrous) and heated to 160° C. At this temperature there is added dropwise thereto within 3 hours a solution of 9.2 g of 2-chloro-5-iodo-nitrobenzene in 75 ml of cyclohexanol (>99%). Subsequently, the reaction solution is held at 160° C. for a further 14 hours. After cooling to room temperature, it is filtered off from inorganic residue and the filtrate is evaporated in vacuo. The evaporation residue is dissolved in 80 ml of hot ethyl acetate and 100 ml of methylene chloride, 2 g of active charcoal are added thereto and the mixture is boiled at reflux for 5 minutes. Thereafter, it is filtered hot and the filtrate is concentrated to 100 ml. There crystallizes rac-(9aβH)-7β(o-fluorophenyl)octahydro-2α-(2-nitro-4-bromo-anilino)-2H-quinolizine. M.p. 175°–177° C. By chromatography of the mother liquor on 150 g of silica gel with n-hexane/diethyl ether 2:1 product is once again obtained.

Where in place of 2-chloro-5-iodo-nitrobenzene correspondingly substituted o-chloro-nitrobenzenes are employed, then the following products are obtained:

|  |  |  | M.p. °C. |
|---|---|---|---|
| R$_a$ = o-fluorophenyl | B = | 2-nitro-4-bromo-anilino | 175–177 |
|  |  | 2-nitro-4-ethoxycarbonyl | 135–140 |
|  |  | 2-nitro-4-cyano | 215–219 |
|  |  | 2-nitro-4-sulfamoyl | 235–237 |

(d) The rac-(9aβH)-7β-(o-fluorophenyl)-2α-(amino)-octahydro-2H-quinolizine employed as the starting material in Example 1c can be obtained as follows:

84.3 g of rac-(9aβH)-7β-(o-fluorophenyl)octahydro-2H-quinolizin-2-one are heated at reflux for 1½ hours in 1700 ml of methanol with 47.4 g of hydroxylamine hydrochloride and 94.3 g of potassium carbonate (anhydrous). Subsequently, the methanol is distilled off and the residue is partitioned between 750 ml of water, 600 ml of chloroform and 150 ml of isopropanol. The aqueous phase is back-extracted twice in each case with 250 ml of a mixture of 200 ml of chloroform and 50 ml of isopropanol, the combined organic phases are dried over magnesium sulfate and subsequently evaporated. There result 85.3 g of oxime which is dissolved in 1.5 l of tetrahydrofuran, 0.5 l of ethanol as well as 1 l of (5% g/g ammonia in ethanol) and hydrogenated with 45 g of Raney-nickel for 30 hours (room temperature, atmospheric pressure). Thereafter, it is filtered off from catalyst and the filtrate is evaporated. From the residue there can be crystallized out by dissolution in 400 ml of ethanol and addition of 130 ml of 5 N hydrogen chloride in ethanol 53.5 g of the dihydrochloride salt of rac-(9aβH)-7β-(o-fluorophenyl)-2α-(amino)octahydro-2H-quinolizine. M.p. 299°–302° C. The diastereomeric rac-(9aβH)-7β-(o-fluorophenyl)-2β-(amino)octahydro-2H-quinolizine is dissolved as the dihydrochloride in the mother liquor.

When in place of rac-(9aβH)-7β-(o-fluorophenyl)-octahydro-2H-quinolizin-2-one correspondingly substituted quinolizidinones are aminated, then the following products are obtained:
rac-(9aβH)-7β—($R_a$)—2α-(amino)octahydro-2H-quinolizine:

$R_a$ = o-chlorophenyl M.p. °C.(0.2HCl): 293°–296° C.

(e) The rac-(9aβH)-7β-(o-fluorophenyl)octahydro-2H-quinolizin-2-one used as the starting material in Example 1d can be obtained as follows:

76.2 g of methyl rac-(1αH,9aβH)-7β-(o-fluorophenyl)-octohydro-2-oxo-2H-quinolizine-1-carboxylate are dissolved in 1.2 l of 4 N hydrochloric acid and boiled at reflux for 7 hours. The cooled reaction solution is subsequently poured on to ice and made alkaline with conc. sodium hydroxide. Extraction with 3×500 l of methylene chloride and evaporation of the organic phase dried over sodium sulfate give 68 g of crude product. From etherhexane there can be recrystallized rac-(9aβH)-7β-(o-fluorophenyl)octahydro-2H-quinolizin-2-one. M.P. 74°–76° C.

When in place of methyl rac-(1αH,9aβH-7β-(o-chlorophenyl)octahydro-2-oxo-2H-quinolizine-1-carboxylate equivalent amounts of correspondingly substituted ketoesters are decarboxylated, the following products are obtained:
rac-(9aβH)-7β-($R_a$)octahydro-2H-quinolizin-2-one:

|  |  | M.p. °C. |
|---|---|---|
| $R_a$ = phenyl |  | 71–72 |
| p-chlorophenyl |  | 80–82 |
| p-trifluoromethylphenyl |  | 103–104 |
| o-methylphenyl | IR(film) | 1726 cm$^{-1}$ |
| m-methoxyphenyl | IR(film) | 1726 cm$^{-1}$ |
| 2,4-dichlorophenyl |  | 116–117 |
| 2,6-dichlorophenyl |  | 116–118 |
| o-chlorophenyl |  | 80–82 |

(f) The octahydro-carboxylate used in Example 1e as the starting material can, in turn, be obtained from the corresponding hexahydro-carboxylate as follows:

180 g of methyl rac-7-(o-fluorophenyl)-3,4,6,7,8,9-hexahydro-2-oxo-2H-quinolizine-1-carboxylate are suspended in 3.6 l of monoglyme (dimethoxyethane), cooled to −30° C. and there are added while stirring 1.33 l of DIBAH (diisobutylaluminium hydride, 20% solution in toluene). Subsequently, the mixture is stirred at −20° to −30° C. for 1 hour and then hydrolyzed at this temperature with 1.72 l of 2 N sodium hydroxide. For the working-up, the mixture is partitioned between 25 l of water and 20 l of chloroform; the organic phase is again washed with 2×5 l of water, dried over magnesium sulfate and evaporated. The crude product is crystallized from etherhexane. By chromatography of the mother liquor on 1 kg of silica gel with ethyl acetate product is once again obtained. There is obtained methyl rac-(1αH,9aβH)-7β-(o-fluorophenyl)-octahydro-2-oxo-2H-quinolizine-1-carboxylate, m.p. 109°–110° C.

When in place of ethyl rac-7-(o-fluorophenyl)-3,5,6,7,8,9-hexahydro-2-oxo-2H-quinolizine-1-carboxylate equimolar amounts of correspondingly substituted educts are reduced with DIBAH, one proceeds to the following compounds:
Methyl rac-(1αH,9aβH)-7β-($R_a$)octahydro-2-oxo-2H-quinolizine-1-carboxylate:

|  |  | M.p. °C. |
|---|---|---|
| $R_a$ = phenyl |  | 114≠116 |
| p-chlorophenyl |  | 102–105 |
| p-trifluoromethylphenyl |  | 108–111 |
| o-methylphenyl |  | 94–98 |
| m-methoxyphenyl | IR(film): | 1752,1723 1660 cm$^{-1}$ |
| 2,4-dichlorophenyl |  | 116–118 |
| 2,6-dichlorophenyl |  | 130–131 |
| o-chlorophenyl |  | 122–124° C. |

(g) The hexahydro-carboxylate used in Example 1f as the starting material can, in turn, be obtained as follows:

150 g of 5-(o-fluorophenyl)-2-piperidone are dissolved in 2 l of methylene chloride and added dropwise at room temperature while stirring within 60 minutes to 410 g of triethyloxonium tetrafluoroborate (Meerwein salt) in 1 l of methylene chloride. Subsequently, the mixture is boiled at reflux for 4 hours and left at room temperature for a further 15 hours. 372 g of potassium carbonate in 370 ml of water are then added dropwise to the solution which is cooled at 0° C., the mixture being stirred intensively. The mixture is left to stir at room temperature for a further 2 hours, the methylene chloride phase is subsequently decanted and the residue is extracted with 2×500 ml of methylene chloride. The methylene chloride phase, dried over potassium carbonate, is concentrated to an oily, partially crystalline residue, then boiled up in 1 l of hexane and filtered hot. From the filtrate there are obtained after evaporation of the hexane, the oily lactim ether: 3-(o-fluorophenyl)-6-ethoxy-2,3,4,5-tetrahydropyridine.

The lactim ether is dissolved in 1.4 l of methanol, 1.3 g of anhydrous p-toluenesulfonic acid are added thereto and 85 g of 3-oxo-5-pentenoic acid methyl ester (Nazarov reagent) are added within 60 minutes. After 20 hours at room temperature, the readily volatile constituents are removed in vacuo, the residue is subsequently taken up in methylene chloride and washed with 500 ml of sat. sodium carbonate solution. The methylene chloride phase, dried over magnesium sulfate, is again concentrated and the residue is crystallized from ethyl acetate-ether=4:1(800 ml). There is obtained methyl rac-7-(o-fluorophenyl)-3,4,6,7,8,9-hexahydro-2-oxo-2H-quinolizine-1-carboxylate. M.p. 165°–167° C.

When in place of 5-(o-fluorophenyl)-2-piperidone equimolar amounts of correspondingly substituted piperidones is used, the following compounds are obtained:
Methyl rac-7-($R_a$)-3,4,6,7,8,9-hexahydro-2-oxo-2H-quinolizine-1-carboxylate:

|  | M.p. °C. |
| --- | --- |
| $R_a$ = phenyl | 148–149 |
| p-chlorophenyl | 185–187 |
| p-trifluoromethylphenyl | 144–145 |
| o-methylphenyl | 183–184 |
| m-methoxyphenyl | 133–134 |
| 2,4-dichlorophenyl | 153–155 |
| 2,6-dichlorophenyl | 159–162 |
| o-chlorophenyl | 145–147° C. |

EXAMPLE 2

Preparation of
rac-1-[(9aβH)-7β-(o-fluorophenyl)octahydro-2H-quinolizin-2α-yl]-2-oxo-5-benzimidazoline carboxylic acid hydrochloride 70 g of rac-1-[(9aβH)-7β-(o-fluorophenyl)octahydro-2H-quinolizin-2α-yl]-2-oxo-5-benzimidazoline carboxylic acid ethyl ester hydrochloride are boiled under reflux for 96 hours in 500 ml of 5 N hydrochloric acid. Subsequently, the mixture is cooled down to 0° C., the reaction product is sucked off over a filter, the residue is washed with 3×100 ml of water and dried in the high vacuum. There results rac-1-[(9aβH)-7β-(o-fluorophenyl)octahydro-2H-quinolizin-2α-yl]-2-oxo-5-benzimidazoline carboxylic acid hydrochloride. M.p. 285°–295° C.

EXAMPLE 3

Preparation of
rac-N-((9aβH)-7β-(o-chlorophenyl)octahydro-2H-quinolizin-2α-yl)-5-sulfamoyl-o-anisamide 4.60 g of 2-methoxy-5-sulfamoyl-benzoic acid are dissolved in 150 ml of methylene chloride and 50 ml of dimethyl sulfoxide and treated at room temperature simultaneously with 2.17 g of chloroformic acid ethyl ester and 2.00 g of triethylamine and stirred for 6 hours. Subsequently, there is added dropwise a solution of 5.30 g of rac-(9αH)-7β-(o-chlorophenyl)-2α-(amino)octahydro-2H-quinolizine in 50 ml of methylene chloride, a further 2.30 g of triethylamine are added and the mixture is left to stir at room temperature for 19 hours. The reaction solution is poured into 1 lt of water and extracted 2 times with 500 ml of methylene chloride each time. The methylene chloride extracts are washed 2 times with 500 ml of water each time and subsequently dried over anhydrous sodium carbonate. After evaporation of the methylene chloride solution, the residue is dissolved in 600 ml of methylene chloride, 400 ml of methanol, 100 ml of ethyl acetate and concentrated by distillation to a volume of 200 ml of solvent. There crystallizes rac-N-((9aβH)-7β-(o-chlorophenyl)octahydro-2H-quinolizin-2α-yl)-5-sulfamoyl-o-anisamide. M.p. 151°–153° C.

Analogously there are obtained
rac-4-amino-5chloro-N-((9aβH)-7β-(o-chlorophenyl)-octahydro-2H-quinolizinquinolizin-2α-yl)-o-anisamide. M.p. 170°–172° C.
rac-N-((9aβH)-7β-(o-chlorophenyl)octahydro-2H-quinolizin-2α-yl)-5-(ethylsulfonyl)-o-anisamide. M.p. 145°–155° C.

EXAMPLE 4

Preparation of
rac-N-((9aβH)-7β-(o-chlorophenyl)octahydro-2H-quinolizin-2α-yl)-p-fluorobenzamide 4.10 g of rac-(9aβH)-7β-(o-chlorophenyl)-2α-(amino)octahydro-2H-quinolizine dissolved in 40 ml of chloroform are treated at 5° C. with vigorous stirring simultaneously with 3.0 g of 4-fluorobenzoyl chloride in 30 ml of chloroform and 0.8 g of sodium hydroxide in 15 ml of water. Subsequently, the mixture is further stirred for 45 minutes at 5° C. and for 60 minutes at room temperature. The reaction mixture is subsequently partitioned between chloroform and water, the chloroform phase is dried over anhydrous sodium carbonate and evaporated. By recrystallization from ethyl acetate there is obtained crystalline rac-N-((9aβH)-7β-(o-chlorophenyl)octahydro-2H-quinolizin-2α-yl)-p-fluorobenzamide. M.P. 200°–202° C.

Analogously there are obtained
rac-N-((9aβH)-7β-(o-chlorophenyl)-ctahydro-2H-quinolizin-2α-yl)cyclopropanecarboxamide. M.p. 193°–195° C.
rac-N-((9aβH)-7β-(o-chlorophenyl)octahydro-2H-quinolizin-2α-yl)-2-thiophenecarboxamide. M.p. 217°–219° C.

EXAMPLE 5

Preparation of
rac-N-((9aαH)-7β-(o-chlorophenyl)octahydro-2H-quinolizin-2α-yl)-2-oxo-1-pyrrolidinecarboxamide 5.30 g of rac-(9aβH)-7β-(o-chlorophenyl)-2α-(amino)octahydro-2H-quinolizine in 100 ml of methylene chloride are added dropwise to 3.56 g of N,N'-carbonyldiimidazole in 100 ml of methylene chloride and subsequently further stirred at room temperature for 2 hours. Then, the reaction mixture is poured into 1 N sodium hydroxide and extracted twice with 300 ml of methylene chloride each time. The organic phase, dried over anhydrous sodium carbonate, is subsequently concentrated. As the intermediate product there is obtained crude rac-N-((9aβH)-7β-(o-chlorophenyl)octahydro-2H-quinolizin-2α-yl)-imidazole-1-carboxamide. The crude intermediate product is treated in 250 ml of toluene with 12.7 g of N-trimethylsilylpyrrolidin-2-one at 80° C. for 17 hours. Subsequently, it is concentrated and the crude reaction mixture is chromatographed over 1 kg of silica gel Merck (0.063-0;2 mm) with chloroform-3% methanol. There is obtained rac-N-((9aβH)-7β-(o-chlorophenyl)octahydro-2H-quinolizin-2α-yl)-2-oxo-1-pyrrolidinecarboxamide, m.p. 184°–186° C.

EXAMPLE 6

Preparation of
rac-N-((9aβH)-7β-(o-chlorophenyl)octahydro-2H-quinolizin-2α-yl)propionanilide 4.20 g of rac-N-((9aβH)-7β-(o-chlorophenyl)-octahydro-2H-quinolizin-2α-yl)aniline dissolved in 100 ml of abs. toluene are treated with 3.4 ml of propionic acid chloride and 3 ml of triethylamine and heated at 80° C. for 6 hours. Subsequently, the reaction solution is partitioned between 2 N sodium hydroxide and chloroform and the aqueous phase is again extracted with chloroform. The organic phase, dried over anhydrous sodium carbonate, is concentrated and chromatographed on a 100 g silica get column with chloroform-1% methanol.

There is eluted rac-N-((9aβH)-7β-(o-chlorophenyl)octahydro-2H-quinolizin-2α-yl)propionanilide which can be recrystallized from ether/n-hexane. M.p. 133°-135° C.

Analogously there is obtained:

rac-4'-chloro-N-((9aβH)-7β-(o-chlorophenyl)octahydro-2H-quinolizin-2α-yl)propionanilide. M.p. (HBr salt): 286°-271° C.

rac-3'-Chloro-N-[(9aβH)-7β-(o-chlorophenyl)-octahydro-2H-quinolizin-2α-yl]-propionanlide. M.p. (base) 124°-126° C.

rac-N-[(9aβH)-7β-(o-Fluorophenyl)-octahydro-2H-quinolizin-2α-yl)-propionanilide. M.p. (HCl salt) 221°-223° C.

rac-4'-Fluoro-N-[9aβH)-7β-(o-fluorophenyl)-octahydro-2H-quinolizin-2α-yl]-propionanilide. M.p. (HCl salt) 240°-242° C.

rac-4'-Fluoro-N-[(9aβH)-7β-phenyl-octahydro-2H-quinolizin-2α-yl]-propionanilide. M.p. (HCl salt) 238°-240° C.

rac-N-[(9aβH)-7β-(o-fluorophenyl)-octahydro-2H-quinolizin-2α-yl]-acetanilide. M.p. (HCl salt) 232°-236° C.

rac-N-[(9aβH)-7β-(o-chlorophenyl)-octahydro-2H-quinolizin-2α-yl]-N-butylpropionamide. M.p. (HCl salt) 175°-177° C.

rac-N-[(9aβH)-7β-phenyl-octahydro-2H-quinolizin-2α-yl]-propionanilide.

The material employed in the above example as the educt can be obtained as follows:

10.5 g of rac-(9aβH)-7β-(o-chlorophenyl)octahydro-2H-quinolizin-2-one are dissolved in 150 ml of methanol, treated "green" with 10 g of molecular sieve 3 A and 5 mg of bromocresol. Subsequently, 4.10 g of aniline are added, 177 g of sodium cyanoborohydride are added thereto and then 2.2 N HCl in methanol (a total of 55 ml) is allowed to flow in dropwise; as the measurement for the velocity of the dropwise addition there is used the bromocresol "green" indicator which is standardized at the transition range green-yellow. After 72 hours reaction time, the mixture is partitioned between 2 N sodium hydroxide and chloroform, the chloroform extract is dried over anhydrous sodium carbonate and evaporated. The crude product is chromatographed on 250 g of silica get, beginning with 1.5 l of ethyl acetate-n-hexane=1:2; with ethyl acetate-n-hexane=1:1 (1 lt) there is eluted the rac-N-((9aβH)-7β-(o-chlorophenyl)octahydro-2H-quinolizin-2α-yl)aniline.

Analogously there is obtained:

rac-4'-chloro-N-((9aβH)-7β-(o-chlorophenyl)octahydro-2H-quinolizin-2α-yl)aniline.

rac-3'-Chloro-N-[(9aβH)-7β-(o-chlorophenyl)-octahydro-2H-quinolizin-2α-yl]aniline.

rac-N-[(9aβH)-7β-(o-Fluorophenyl)-octahydro-2H-quinolizin-2α-yl]aniline.

rac-4'-Fluoro-N-[(9aβH)-7β-(o-fluorophenyl-octahydro-2H-quinolizin-2α-yl]aniline.

rac-4'-Fluoro-N-[(9aβH)-7β-phenyl-octahydro-2H-quinolizin-2α-yl]aniline.

rac-N-[(9αβH)-7β-(o-Fluorophenyl)-octahydro-2H-quinolizin-2α-yl]aniline.

rac-N-[(9aβH)-7β-(o-Chlorophenyl)-octahydro-2H-quinolizin-2α-yl]aniline.

rac-N-[(9aβH)-7β-phenyl-octahydro-2H-quinolizin-2α-yl]aniline.

EXAMPLE 7

Preparation of rac-(9aβH)-7β-(o-chlorophenyl)octahydro-2H-quinolizin-2α-yl)p-fluorophenyl ketone 14.5 g of p-fluorobenzyl-triphenyl-phosphonium chloride are suspended in 100 ml of abs. diethyl ether and treated at 0° C. with 20 ml of n-butyl lithium (1.8 molar) and stirred at 0°-5° C. for 1 hour. Subsequently, there is added dropwise thereto a solution of 8.8 g of rac-(9aβH)-7β-(o-chlorophenyl)octahydro-2H-quinolizin-2-one in 150 ml of abs. diethyl ether and then the mixture is heated at reflux temperature for 4 hours. The cooled solution is hydrolyzed with 30 ml of saturated ammonium chloride solution and then partitioned between ethyl acetate and 0.5 N sodium hydroxide. The ethyl acetate phase, dried over anhydrous magnesium sulfate, is evaporated and chromatographed over 100 g of silica gel with ethyl acetate-n-hexane=1:1. An oily E/Z mixture of rac-(9aβH)-7β-(o-chlorophenyl)-2-((p-fluorophenyl)methylene)octahydro-2H-quinolizine is eluted. This mixture is dissolved in 115 ml of ethyleneglycol dimethyl ether (dried neutral over aluminum oxide, activity grade I), treated with 1.77 g of sodium borohydride and there is added dropwise at room temperature a solution of 11.5 g of boron trifluoride etherate in 77 ml of ethyleneglycoldimethyl ether. After 1 hours stirring at room temperature, the mixture is cooled down to 0°-5° C. and there is cautiously added dropwise a solution of 1.23 g of potassium hydroxide in 50 ml of water and subsequently 4.6 ml of hydrogen peroxide (60%) and then the mixture is heated at reflux temperature. The cooled reaction mixture is partitioned between 2 N sodium hydroxide and ethyl acetate, the organic phase is dried over anhydrous magnesium sulfate and evaporated to dryness. This crude product is dissolved in 240 ml of acetone, cooled to 0°-5° C. and 32 ml of Jones reagent (manufactured from 80 g of chromium trioxide, 64 ml of conc. sulfuric acid, 300 ml of water) are added dropwise thereto and the mixture is stirred at 0°-5° C. for 1 hour. Subsequently, the reaction mixture is partitioned between 150 ml of sat. sodium acetate solution and 250 ml of ethyl acetate as well as 200 ml of 2 N sodium hydroxide. The organic phase, dried over anhydrous magnesium sulfate, is evaporated to dryness. The crude product is again dissolved in 30 ml of ethyl alcohol and treated with 0.3 g of sodium ethylate. After 3 hours stirring at room temperature, the mixture is partitioned between 2 N sodium hydroxide and ethyl acetate, the organic phase is dried over anhydrous magnesium sulfate, treated with 1 g of active charcoal and warmed to 50° C., filtered off and evaporated to dryness. By crystallization from ethyl alcohol-ethyl acetate there is obtained rac-(9aβH)-7β-(o-chlorophenyl)octahydro-2H-quinolizin-2α-yl) p-fluorophenyl ketone (m.p. 145°-147° C.). From the mother liquor there can be obtained by chromatography on 100 g of silica gel with ethyl acetate a further fraction of product. HCl salt (from methylene chloride-ethyl acetate) m.p.: 256°-258° C.

EXAMPLE 8

| Tablets | Per tablet |
|---|---|
| rac-(9aβH)—7β-(o-Chlorophenyl)-octahydro-2H—quinolizin-2α-yl)p-fluorophenyl ketone.HCl | 100 mg |

| Tablets | Per tablet |
|---|---|
| Lactose | 202 mg |
| Maize starch | 80 mg |
| Hydrolyzed maize starch | 20 mg |
| Calcium strearate | 8 mg |
| Total weight | 410 mg |

The active substance, the lactose, the maize starch and the hydrolyzed maize starch are mixed and granulated withh water to a viscous paste. This paste is passed through a sieve and subsequently dried at 45° C. overnight. The dried granulate is passed through a sieve and subsequently mixed with the calcium stearate. The mixture obtained is pressed to tablets of a weight of 410 mg and with a diameter of about 10 mm.

EXAMPLE 9

| Tablets | Per tablet |
|---|---|
| rac-1-[(9aβH)—7β-(o-Fluorophenyl)-octahydro-2H—quinolizin-2α-yl]-5-bromo-2-benzimidazolinone.HCl | 10.0 mg |
| Lactose | 129.0 mg |
| Maize starch | 50.0 mg |
| Gelatinized maize starch | 8.0 mg |
| Calcium stearate | 3.0 mg |
| Total weight | 200.0 mg |

The active substance, the lactose, the maize starch and the gelatinized maize starch are intimately mixed with one another. The mixture is passed through a comminuting machine and subsequently moistened with water to a thick paste. The moist mass is passed through a sieve. The moist granulate is dried at 45° C. The dried granulate is mixed thoroughly with the calcium stearate. The granulate is now pressed to tablets of a weight of 200 mg and a diameter of about 8 mm.

EXAMPLE 10

| Tablets | Per tablet |
|---|---|
| rac-1-[(9aβH)—7β-(o-Fluorophenyl)-octahydro-2H-quinolizin-2α-yl]-5-iodo-2-benzimidazolinone.HCl | 10.0 mg |
| Lactose | 129.0 mg |
| Maize starch | 50.0 mg |
| Gelatinized maize starch | 8.0 mg |
| Calcium stearate | 3.0 mg |
| Total weight | 200.0 mg |

The active substance, the lactose, the maize starch and the gelatinized maize starch are intimately mixed with one another. The mixture is passed through a comminuting machine and subsequently moistened with water to a thick paste. The moist mass is passed through a sieve. The moist granulate is dried at 45° C. The dried granulate is thoroughly mixed with the calcium stearate. The granulate is now pressed to tablets of a content of 200 mg and a diameter of about 8 mm.

EXAMPLE 11

| Tablets | Per tablet |
|---|---|
| rac-N—((9aβH)—7α-(o-chlorophenyl)-octahydro-2H-quinolizin-2α-yl)-propionanilide.HBr | 20.0 mg |
| Lactose | 115.0 mg |
| Maize starch | 61.0 mg |
| Talc | 3.4 mg |
| Magnesium stearate | 0.6 mg |
| Total weight | 200.0 mg |

The ingredients are inimately mixed with one another and pressed to tablets each of 200 mg. Subsequently, they are coated with ethyl cellulose and Carbowax.

EXAMPLE 12

| Capsules | Per capsule |
|---|---|
| rac-1-[(9aβH)—7β-(o-Fluorophenyl)-octahydro-2h—quinolizin-2αyl]-5-bromo-2-benzimidazolinone.HCl | 10.0 mg |
| Lactose | 175.0 mg |
| Maize starch | 30.0 mg |
| Talc | 5.0 mg |
| Total weight | 220.0 mg |

The active substance, the lactose and the maize starch are intimately mixed with one another and passed through a comminuting machine. The mixture is now thoroughly mixed with the talc and filled into hard gelatin capsules.

EXAMPLE 13

| Capsules | Per capsule |
|---|---|
| rac-N—((9aβH)—7β-(o-Chlorophenyl)-octahydro-2H—quinilozin-2α-yl)-propionanilide | 10.0 mg |
| Lactose | 175.0 mg |
| Maize starch | 30.0 mg |
| Talc | 5.0 mg |
| Total weight | 220.0 mg |

The active substance, the lactose and the maize starch are intimately mixed with one another and passed through a comminuting machine. The mixture is now mixed thoroughly with the talc and filled into hard gelatin capsules.

EXAMPLE 14

| Each 1 ml ampoule contains: | |
|---|---|
| rac-1-[(9aβH)—7β-(o-Fluorophenyl)-octahydro-2H—quinolizin-2α-yl]-5-bromo-2-benzimidazolinone.HCl | 0.204 mg (2% excess) |
| Glucose for injection | 40.0 mg |
| Water for injection q.s. ad | 1.0 mg |

2.04 g of active substance are treated with 400 g of glucose, dissolved in water for injection and made up to a volume of 10,000 ml with water for injection. The solution is either filtered sterile, filled into colorless ampules, gassed with nitrogen and sealed or filled into colorless ampules, gassed with nitrogen, sealed and subsequently sterilized for 30 minutes with flowing steam or autoclaved at 120° C.

EXAMPLE 15

| Parenteral preparation form (0.5 mg) Each 1 m. ampoule contains: | |
|---|---|
| rac-N—((9aβH)—7β-(o-Chlorophenyl)octahydro-2H-quinolizin-2αyl)propionanilide | 0.510 mg (2% excess) |
| Glucose for injection | 40.0 mg |
| Water for injection q.s. ad | 1.0 ml |

510 g of active substance are treated with 400 g of glucose, dissolved in water for injection and made up to a volume of 10,000 ml with water for injection. The solution is either filtered sterile, filled into colorless ampules, gassed with nitrogen and sealed or filled into colorless ampules, gassed with nitrogen, sealed and subsequently sterilized for 30 minutes with flowing steam or autoclaved at 120° C.

We claim:

1. A compound of the formula

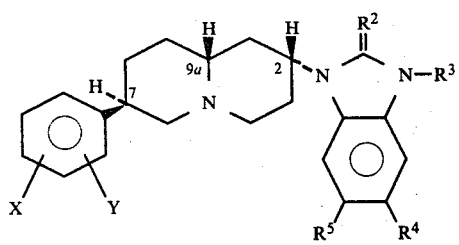

wherein X is hydrogen, fluorine, chlorine, lower-alkoxy, lower-alkyl or trifluoromethyl; Y is hydrogen, fluorine, chlorine, lower-alkoxy, or lower-alkyl; $R^2$ is oxygen or sulfur; $R^3$ is hydrogen or lower-alkyl; and one of $R^4$ and $R^5$ is hydrogen and the other is bromine, iodine, cyano, lower-alkoxycarbonyl or sulfamoyl in the form of its racemate or its enantiomers, as well as a pharmaceutically acceptable acid addition salt thereof.

2. A compound in accordance with claim 1, which is rac-1-[(9aβH)-7β-(o-Fluorophenyl)-octahydro-2H-quinolin-2α-yl]-5-bromo-2-benzimidazolinone in the form of its racemate or its enantiomers, as well as a pharmaceutically acceptable acid addition salt thereof.

3. A compound, in accordance with claim 1, which is rac-1-[(9aβH)-7β-(o-Fluorophenyl)-octahydro-2H-quinolizin-2α-yl]-5-iodo-2-benzimidazolinone in the form of its racemate or its enantiomers, as well as a pharmaceutically acceptable acid addition salt thereof.

4. A compound, in accordance with claim 1, which is rac-1-[(9aβH)-7β-(o-Fluorophenyl)-octahydro-2H-quinolizin-2α-yl]-5-cyano-2-benzimidazolinone in the form of its racemate or its enantiomers, as well as a pharmaceutically acceptable acid addition salt thereof.

5. A compound of the formula

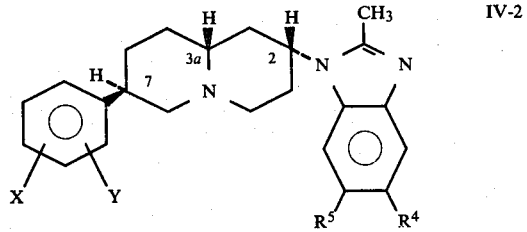

wherein X is hydrogen, fluorine, chlorine, lower-alkoxy, lower-alkyl or trifluoromethyl; Y is hydrogen, fluorine, chlorine, lower-alkoxy or lower-alkyl; and one of $R^4$ and $R^5$ is hydrogen and the other is bromine, iodine, cyano, lower-alkoxycarbonyl or sulfamoyl, in the form of its racemate or its enantiomers, as well as a pharmaceutically acceptable acid addition salt thereof.

* * * * *